United States Patent [19]
Alvarez et al.

[11] Patent Number: 5,280,323
[45] Date of Patent: Jan. 18, 1994

[54] DEVELOPMENT APPARATUS EMPLOYING MAGNETIC FIELD SHAPERS

[75] Inventors: Jorge A. Alvarez, Rochester; Gary A. Denton, Webster; Peter J. McGuire, Rochester; Francisco Zirilli, Walworth, all of N.Y.

[73] Assignee: Xerox Corporation, Stamford, Conn.

[21] Appl. No.: 814,171

[22] Filed: Dec. 30, 1991

Related U.S. Application Data

[63] Continuation-in-part of Ser. No. 757,100, Sep. 10, 1991.

[51] Int. Cl.⁵ .................................... G03G 15/09
[52] U.S. Cl. ........................... 355/251; 118/658; 355/253; 430/122
[58] Field of Search .............. 355/245, 251, 253, 215; 118/656, 657, 658; 430/122, 45

[56] References Cited

U.S. PATENT DOCUMENTS

| | | | |
|---|---|---|---|
| 3,626,898 | 12/1971 | Gawron | 118/637 X |
| 4,078,929 | 3/1978 | Gundlach | 96/1.2 |
| 4,292,924 | 10/1981 | Lindblad et al. | 118/658 |
| 4,320,958 | 3/1982 | Fantuzzo | 355/270 |
| 4,517,719 | 5/1985 | Okumura et al. | 29/124 |
| 4,638,759 | 1/1987 | Ville et al. | 118/657 |
| 4,640,808 | 2/1987 | Okumura et al. | 264/46.5 |
| 4,641,946 | 2/1987 | Forbes, II | 355/251 |
| 4,724,457 | 2/1988 | Abreu et al. | 118/657 X |
| 4,811,046 | 3/1989 | May | 355/4 |
| 4,816,870 | 3/1989 | Nagayama | 355/251 |
| 4,829,338 | 5/1989 | Whittaker et al. | 355/305 |
| 4,833,504 | 5/1989 | Parker et al. | 355/326 |
| 4,878,089 | 10/1989 | Guslites et al. | 355/253 |
| 4,972,231 | 11/1990 | Bares | 355/251 |
| 5,052,336 | 10/1991 | Fukuchi | 118/658 |
| 5,063,412 | 11/1991 | Hirsch | 355/259 |

Primary Examiner—Leo P. Picard
Assistant Examiner—Christopher Horgan

[57] ABSTRACT

An electrophotographic printing machine in which an electrostatic latent image is recorded on a photoconductive surface by charging the appropriate areas of the surface to predetermined polarities. The latent image is a developed with toners of a preselected color and predetermined polarity by a developer unit. The developer unit includes a bead removal device which magnetically attracts carrier beads off the photoconductive surface and deposits these beads in a sump or reservoir of developer. The bead removal device includes a magnet and magnetic field shapers to enhance the magnetic fields which attract the beads in the zone between the surface and the bead removal device and attenuates the magnetic fields in the zone between the bead removal device and the sump or reservoir to reduce the attraction between the beads and the bead removal device in this zone. The invention also provides magnetic brush rollers for the delivery of toner to the photoconductive surface which have magnetic field shapers which attenuate the magnetic fields to encourage bead release from the roller and reduce attraction of beads to the roller in reverse rotation of the roller.

18 Claims, 7 Drawing Sheets

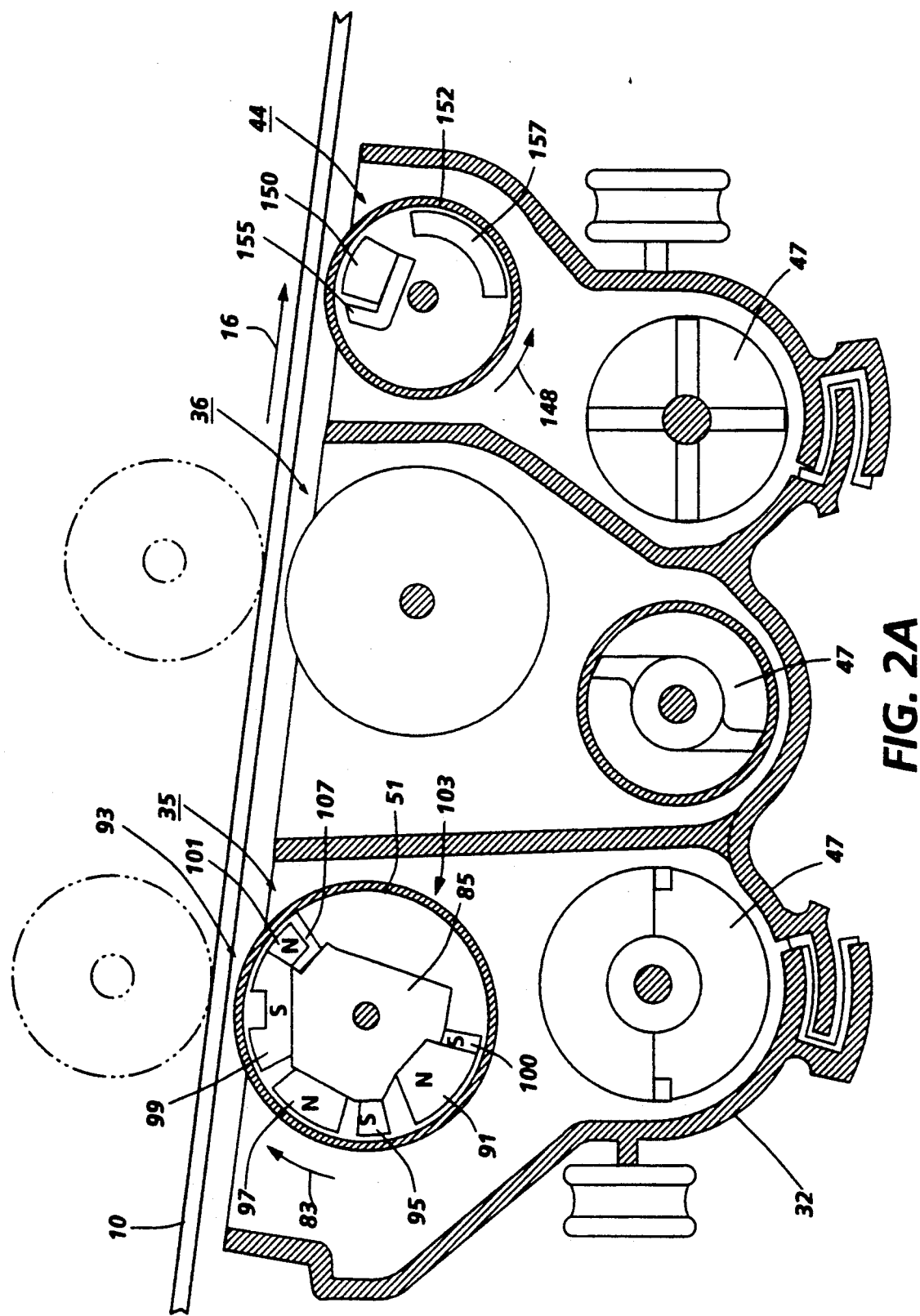

DEVELOPMENT APPARATUS EMPLOYING MAGNETIC FIELD SHAPERS

This application is a continuation-in-part of U.S. application Ser. No. 757,100, which was filed on Sep. 10, 1991 and which is assigned to the same assignee as the present application.

This invention relates generally to an electrophotographic printing machine adapted to produce highlight color and monochromatic copies, and more particularly concerns a development system having at least one developer unit which employs ferromagnetic carriers in the delivery of toner to a photoconductive surface.

INCORPORATION BY REFERENCE

The following are incorporated herein by reference: U.S. Pat. No. 4,829,338, and U.S. Pat. No. 4,811,046

BACKGROUND OF THE INVENTION

The features of the present invention may be used in the printing arts and more particularly in electrophotographic printing. In the process of electrophotographic printing, a photoconductive surface is charged to a substantially uniform potential. The photoconductive surface is image wise exposed to record an electrostatic latent image corresponding to the informational areas of an original document being reproduced. This records an electrostatic latent image on the photoconductive surface corresponding to the informational areas contained within the original document. Thereafter, a developer material is transported into contact with the electrostatic latent image in a region known as the development zone. Toner particles are attracted from carrier granules or bead carriers of the developer material onto the latent image. The resultant toner powder image is then transferred from the photoconductive surface to a copy sheet and permanently affixed thereto. The foregoing generally describes a typical mono-color electrophotographic copying machine.

Recently, electrophotographic printing machines have been developed which produce highlight color copies. A typical highlight color printing machine records successive electrostatic latent images on the photoconductive surface. When combined, these electrostatic latent images form a total latent image corresponding to the entire original document being reproduced.

One latent image is usually developed with black toner particles. The other latent image is developed with color highlighting toner particles, e.g. red toner particles. These developed toner images are transferred sequentially to the copy sheet to form the color highlighted copy. A color highlight printing machine of this type is a two pass machine.

Single pass highlight color printing machines using tri-level printing have also been developed. Tri-level electrophotographic printing is described in detail in U.S. Pat. No. 4,078,929. As described in this patent, the latent image is developed with toner particles of first and second colors. The toner particles of one of the colors are positively charged and the toner particles of the other color are negatively charged. In one embodiment, the toner particles are supplied by a developer which comprises a mixture of triboelectrically relatively positive and relatively negative carrier beads. The carrier beads support, respectively, the relatively negative and relatively positive toner particles. Such a developer is generally supplied to the charge pattern by cascading it across the imaging surface supporting the charge pattern. In another embodiment, the toner particles are presented to the charge pattern by a pair of magnetic brushes. Each brush supplies a toner of one color and one charge. In yet another embodiment, the development system is biased to about the background voltage. Such biasing results in a developed image of improved color sharpness.

In tri-level electrophotographic printing, the charge on the photoconductive surface is divided in three, rather than two, ways as is the case in mono-color printing. The photoconductive surface is charged, typically to about 900 volts. It is exposed image wise, such that one image corresponding to charged image areas remains at the full potential of 900 volts. The other image, which corresponds to discharged image areas is exposed to discharge the photoconductive surface to its residual potential of typically about 100 volts. The background areas are exposed to reduce the photoconductive surface potential to about halfway between the charged and discharged potentials, (typically about 500 volts). The developer unit arranged to develop the charged image areas, is typically biased to about 600 volts, and the developer unit, arranged to develop the discharged image areas, is biased to about 400 volts.

The single pass nature of this system dictates that the electrostatic latent image pass through the developer units in a serial fashion. When the latent image, which has a high charged image potential region and a low charge image potential region, passes through the first developer unit, arranged to develop the discharged image areas, an extremely high cleaning field potential is established between the electrically biased developer unit and the highly charged image areas of the latent image. This high cleaning field potential attracts developer material from the developer unit onto the highly charged image areas. When this occurs, the highly charged image areas of the electrostatic latent image are locally discharged where developed, and as a result, white spots will be noticeable in the solid area images developed by the second developer unit, which at the present time is black, rendering the prints unacceptable.

This problem was overcome by the invention disclosed in the below-referenced co-pending U.S. application Ser. No. 07/604,269. However, electrostatic forces and adhesion forces within the developer units contribute to a condition where the bead carriers are carried out of the development unit. Bead removal devices (BRDs) are well known and commonly used to pick off any developer carriers which are carried out of the development zone of a development unit.

Generally BRDs operate by generating a strong magnetic field in the area between the photoconductive surface and the BRD to attract free bead carriers to the shell of the BRD. These captured beads are then deposited in a sump or developer receiver as the shell of the BRD is rotated. This arrangement, however, renders release of beads from the BRD more difficult, e.g. gravity and centripetal forces often are insufficient to achieve release of the beads from the magnetic field as the shell of the BRD rotates. That is the strong magnetic field necessary to attract bead carriers from the photoconductive surface to the BRD shell are sufficiently strong around the shell itself to retain some bead carriers as the shell rotates.

As disclosed in U.S. Pat. No. 4,829,338, the magnetic field from the magnet positioned in the shell of the BRD can be directed by use of a ferromagnetic shunt to promote bead removal from the photoconductive surface while enhancing the field between the photoconductive surface and the BRD to attract free beads. Nevertheless, this solution has not overcome all problems associated with BRDs.

Specifically, some bead carriers remain attached to the shell as the shell rotates. These unreleased beads tend to attract additional beads to themselves to form bead chains. These bead chains can span the gap between the BRD and photoconductive surface causing degradation of the image being reproduced. For example, in highlight color electrographic printing machines, when bead chains occur in the first discharged developer unit, portions of the second latent image which are contacted by the chains are discharged thereby causing discharge line defects in the finished print.

Also, the arrangement disclosed in U.S. Pat. No. 4,829,338 does not address carrier pickup and carry through in reverse rotation of a BRD. In highlight color electrographic printing machines using magnetic delivery means, monochromatic images are often achieved by disabling one of the developer units. One technique is to reverse the direction of the magnetic brush rollers as disclosed in U.S. Pat. No. 4,811,046 to May, which is incorporated by reference herein. The reversal of the direction of travel of the rollers in the developing units in this case effects a substantial reduction in developer available to effect the charged photoconductive surface. Such reversal of angular travel of the rollers can also be done during warm-up and shut down cycles to remove stray or extraneous developer materials from the developer zone. However, reversed rotation of the rollers is not entirely satisfactory, as some beads are not released and certain other beads are attracted to and attach to the roller. Failure to release the beads, as well as the attraction of additional beads, results, for example, in discharge of portions of the latent image on the photoconductive surface as it passes through a developer unit to a secondary developer unit.

During ordinary operation some beads fail to release from the roller. When this involves a substantial number of beads, a condition mimicking a low toner condition results. Essentially, empty beads are being transported through the development zone and insufficient toner is delivered to develop the latent image.

Optimally the magnetic field at the release point of development rollers must be minimized to reduce carry through of 'empty' beads and to prevent carry back of beads in the "reversed" rotating rollers. Further, this must be accomplished without substantially affecting the magnetic field characteristics along the remainder of the rollers which are responsible for bead pickup, bead transport, bead timing, developing by toner, migration from bead to photoconductive surface and carry out of beads from development zone. Also, the magnetic fields around a BRD housing must be maximized along the interface between the BRD shell and the photoconductive surface and minimized at all other points to afford return of released beads to a sump or reservoir and to impede bead chain formation.

Various techniques have heretofore been used to develop electrostatic latent images as illustrated by the following disclosures, which may be relevant to certain aspects of the present invention:

U.S. Pat. No. 4,320,958
Patentee: Fantuzzo
Issued: Mar. 23, 1982

U.S. Pat. No. 4,641,946
Patentee: Forbes II
Issued: Feb. 10, 1987

U.S. Pat. No. 4,833,504
Patentee: Parker et al.
Issued: May 23, 1989

Co-pending U.S. application Ser. No. 07/604,269
Applicant: Hogestyn
Filed: Oct. 29, 1990

The relevant portions of the foregoing patents may be briefly summarized as follows:

U.S. Pat. No. 4,320,958 discloses a processing station for an electrophotographic printing which cleans the photoconductive surface and develops an electrostatic latent image recorded thereon. The processing unit uses an indexable magnet positioned interiorly of a rotating tubular sleeve. During development, the magnet is indexed so that a weak magnetic field is generated in the development zone during development. During cleaning, the magnet is indexed to generate a strong magnetic field in the cleaning zone.

U.S. Pat. No. 4,641,946 describes a developer roller having a rotating tubular sleeve with a magnet disposed interiorly thereof. A photoconductive belt is wrapped about a portion of the exterior surface of the sleeve. The magnet generates a radial magnetic field in the development zone which, at the center, may range from 0 gauss to 500 gauss. FIG. 4 shows a radial magnetic field, in the development zone, having a valley of about $-185$ gauss and twin peaks, each of about $-385$ gauss.

U.S. Pat. No. 4,833,504 discloses a single pass highlight color electrophotographic printing machine using two developer units. The first developer unit contains developer with black toner. The black toner is driven to the most highly charged areas of the latent image by the electrostatic field between the photoreceptor and developer rolls. The second developer unit contains developer with the highlight color toner. The highlight color toner is urged towards the parts of the latent image at the residual potential, i.e. the discharged region of the latent image, by the electrostatic field between the photoreceptor and the development rolls in the second housing. The magnetic rolls in the second developer unit are constructed such that the radial component of the magnetic force field produces a magnetically free development zone intermediate a charge retentive surface and the magnetic rolls. The developer is moved through the zone magnetically unconstrained and subjects the image developed by the first developer unit to minimal disturbance. In addition, the developer is transported from one magnetic roll to the next.

Co-pending U.S. patent application Ser. No. 07/604,269 describes an electrophotographic printing machine in which an electrostatic latent image is recorded on a photoconductive surface. One portion of the latent image is a discharged area with the other portion of the latent image being a charged area. The discharged image area is developed with toner particles of a first color and polarity by a first developer unit. The first developer unit generates a weak magnetic field in the development zone and a strong magnetic field at the entrance and exit of the development zone. A second developer unit develops the charged image area with toner of a second color and polarity. The colors of the toners are different from one another.

In accordance with one aspect of the present invention, there is provided a developer unit for use in an electrographic printing device of the type having a latent image recorded on a moving charge retentive surface. The unit includes a developer roller for developing the latent image with toner of predetermined polarity. The developer roller includes a rotatable outer housing, fixed magnetic means disposed within said housing, and ferromagnetic field shaping means disposed within the housing to shape the magnetic fields induced by the magnetic means disposed within said housing. Specifically, the magnetic means and the field shaping means are arranged so bead carriers are attracted and adhere to the outer housing of developer shell for delivery of toner in a development zone and then are released from the shell. Also, the means are arranged so that upon reversal of the roller, the bead carriers do not adhere to the roller for passage through the development zone.

Pursuant to another aspect of the present invention, there is provided a developer unit in an electrographic printing device of the type having an electrostatic latent image recorded on a moving charge retentive surface. The developer unit includes means for developing the latent image with toner of predetermined polarity. The developer unit also includes a bead removal device having a rotatable outer shell and fixed magnetic means positioned within the shell. A first magnetic shunt is disposed in the shell to shape the magnetic field to urge capture of any beads passing between the photoconductive surface and the bead removal device and to urge release of such captured carriers into a sump as the shell rotates. A second magnetic shunt is positioned in the shell to shape the magnetic field to minimize the magnetic fields on a portion of the shell to inhibit bead chain formation. Further, the second magnetic shunt is also positioned to shape the magnetic field to urge release of beads captured during reverse rotation of the BRD shell.

According to yet another aspect of the present invention, there is provided a developer unit in an electrographic printing device of the type having an electrostatic latent image recorded on a moving charge retentive surface. The developer unit includes means for developing the latent image with toner of predetermined polarity. The developer unit also includes a bead removal device having a rotatable outer shell and fixed magnetic means positioned within the shell. A first magnetic shunt is disposed in the shell to shape the magnetic field to urge capture of any beads passing between the photoconductive surface and the bead removal device and to urge release of such captured carriers into a sump as the shell rotates. A second magnetic shunt is positioned in the shell to shape the magnetic field to minimize the magnetic fields on a portion of the shell. The bead removal device may also be connected to an AC power source, and the shell of the magnetic means can be two magnets of substantially opposite polarity orientation.

Other features of the present invention will become apparent as the following description proceeds and upon reference to the drawings, in which:

FIGS. 2a and 2b are elevational views showing the developer units and a portion of the photoconductive surface of the FIG. 1 printing machine;

While the present invention will be described in connection with a preferred embodiment thereof, it will be understood that it is not intended to limit the invention to that embodiment. On the contrary, it is intended to cover all alternatives, modifications, and equivalents as may be included within the spirit and scope of the invention as defined by the appended claims.

Figure 1:
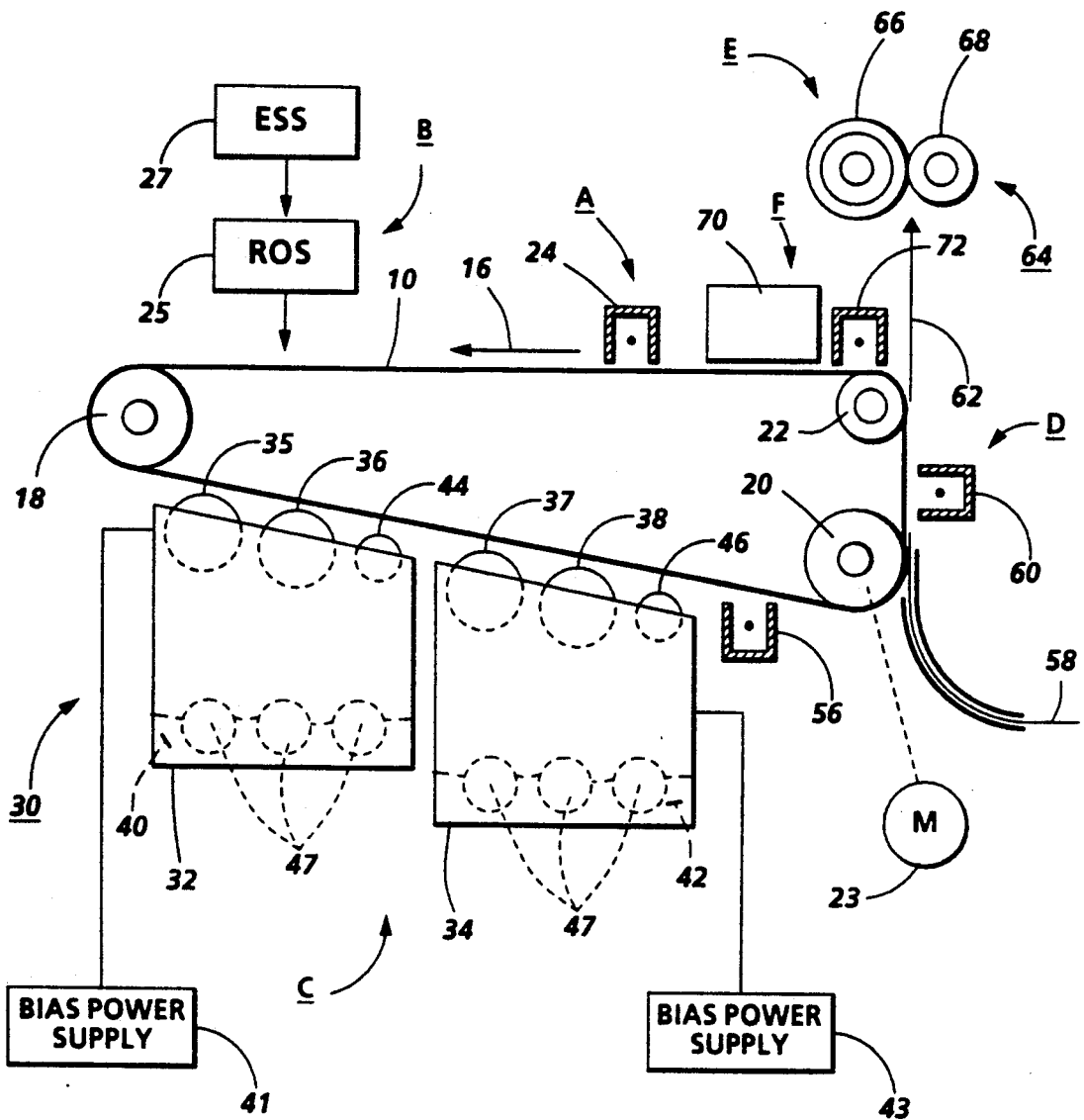
FIG. 1 is a schematic elevational view of an illustrative electrophotographic printing machine incorporating the developer units of the present invention therein.

For a general understanding of the illustrative electrophotographic printing machine incorporating the features of the present invention therein, reference is made to the drawings. In the drawings, like reference numerals have been used throughout to designate identical elements. FIG. 1 schematically depicts the various components of an electrophotographic printing machine incorporating the developer units of the present invention therein. Although the developer units of the present invention are particularly well adapted for use in the illustrative printing machine, it will become evident that these developer units are equally well suited for use in a wide variety of printing machines and are not necessarily limited in their application to the particular embodiments shown herein.

Referring now to FIG. 1, the electrophotographic printing machine employs a belt 10, i.e. a charge retentive member, having a photoconductive surface deposited on a conductive substrate. Preferably, the photoconductive surface is made from a selenium alloy with the conductive substrate being made preferably from an electrically grounded aluminum alloy. Belt 10 moves in the direction of arrow 16 to advance successive portions thereof sequentially through the various processing stations disposed about the path of movement thereof. Belt 10 is entrained about drive roller 20, tensioning roller 18 and stripping roller 22. Motor 23 rotates roller 20 to advance belt 10 in the direction of arrow 16. Roller 20 is coupled to motor 23 by suitable means such as a belt drive.

Initially successive portions of belt 10 pass through charging station A. At charging station A, a corona generating device, indicated generally by the reference numeral 24, charges the belt 10 to a selectively high uniform positive or negative potential. Preferably the charging is to a negative potential. Any suitable control, well known in the art, may be employed for controlling the corona generating device 24.

Next, the charged portions of the photoconductive surface are advanced through exposure station B. At exposure station B, the uniformly charged photoconductive surface or charge retentive surface is exposed to a laser based input and/or output scanning device 25 which causes the charge retentive surface to be selectively discharged in accordance with the output from the scanning device. Preferably the scanning device is a three level laser Raster Output Scanner (ROS). Alternatively, the ROS could be replaced by a conventional xerographic exposure device. The photoconductive surface, which is initially charged to a high charge potential, is discharged image wise in the background (white) image areas and to near zero or ground potential in the highlight (i.e. color other than black) color parts of the image.

At development station C, a magnetic brush development system, indicated generally by the reference numeral 30 advances developer materials into contact with the electrostatic latent images. The development system 30 comprises first and second developer units 32 and 34. Preferably, each magnetic brush developer units includes a pair of magnetic brush developer rollers mounted in a housing. Thus, developer unit 32 contains a pair of magnetic brush rollers 35, 36 with developer unit 34 containing a pair of magnetic brush rollers 37, 38. Each pair of rollers advances its respective developer material into contact with the latent image. Appropriate developer biasing is accomplished via power supplies 41 and 43 electrically connected to respective developer units 32 and 34.

Color discrimination in the development of the electrostatic latent image is achieved by moving the latent image recorded on the photoconductive surface past two developer units 32 and 34 in a single pass with the magnetic brush rolls 35, 36, 37 and 38 electrically biased to voltages which are offset from the background voltage, the direction of offset depending on the polarity of toner in the housing. The first developer unit 32, in the direction of movement of belt 10 as indicated by arrow 16, develops the discharged image areas of the photoconductive surface. This developer unit contains, for example, red developer material 40 having triboelectric properties such that the red toner is driven to the discharged image areas of the latent image by the electrostatic field between the photoconductive surface and the electrically biased developer rolls. Conversely, the second developer unit 34, in the direction of movement of belt 10 as indicated by arrow 16, develops the highly charged image areas of the latent image. This developer unit contains black developer, for example, material 42 having a triboelectric charge such that the black toner is urged towards highly charged areas of the latent image by the electrostatic field existing between the photoconductive surface and the electrically biased developer rolls in the second developer unit. Further, the first and second developer units 32 and 40 have bead removal devices 44 and 46 disposed therein and augers 47 for mixing and charging the developer material.

A sheet of support material 58 is moved into contact with the toner image at transfer station D. The sheet of support material is advanced to transfer station D by conventional sheet feeding apparatus, not shown. Preferably, the sheet feeding apparatus includes a feed roll contacting the uppermost sheet of a stack copy sheets. Feed rolls rotate so as to advance the uppermost sheet from stack into a chute which directs the advancing sheet of support material into contact with the photoconductive surface of belt 10 in a timed sequence so that the toner powder image developed thereon contacts the advancing sheet of support material at transfer station D.

Because the composite image developed on the photoreceptor consists of both positive and negative toner, a negative pre-transfer corona generating device 56 is provided to condition the toner for effective transfer to a substrate using positive corona discharge.

Transfer station D includes a corona generating device 60 which sprays ions of a suitable polarity onto the backside of sheet 58. This attracts substantially simultaneously the black and non-black portions of the toner powder image from the belt 10 to sheet 58. After transfer, the sheet continues to move, in the direction of arrow 62, onto a conveyor (not shown) which advances the sheet to fusing station E.

Fusing station E includes a fuser assembly, indicated generally by the reference numeral 64, which permanently affixes the transferred powder image to sheet 58. Preferably, fuser assembly 64 comprises a heated fuser roller 66 and a pressure roller 68. Sheet 58 passes between fuser roller 66 and pressure roller 68 with the toner powder image contacting fuser roller 66. In this manner, the toner powder image is permanently affixed to sheet 58. After fusing, a chute, not shown, guides the advancing sheet 58 to a catch tray, also not shown, for subsequent removal from the printing machine by the operator.

After the sheet of support material is separated from photoconductive surface of belt 10, the residual toner particles carried by the non-image areas on the photoconductive surface are charged to a suitable polarity and level by a preclean charging device 72 to enable removal therefrom. These particles are removed at cleaning station F. The vacuum assisted, electrostatic, fur brush cleaner unit 70 is disposed at the cleaner station F. The cleaner unit has two fur brush rolls that rotate at relatively high speeds which creates mechanical forces that tend to sweep the residual toner particles into an air stream (provided by a vacuum source), then into a cyclone separator, and finally into a waste bottle. In addition, the brushes are triboelectrically charged to a very high negative potential which enhances the attraction of the residual toner particles to the brushes and increases the cleaning performance.

Subsequent to cleaning, a discharge lamp (not shown) floods the photoconductive surface with light to dissipate any residual electrostatic charge remaining prior to the charging thereof for the successive imaging cycle.

It is believed that the foregoing description is sufficient for purposes of the present application to illustrate the general operation of an electrophotographic printing machine incorporating the development apparatus of the present invention therein.

Figure 2B:
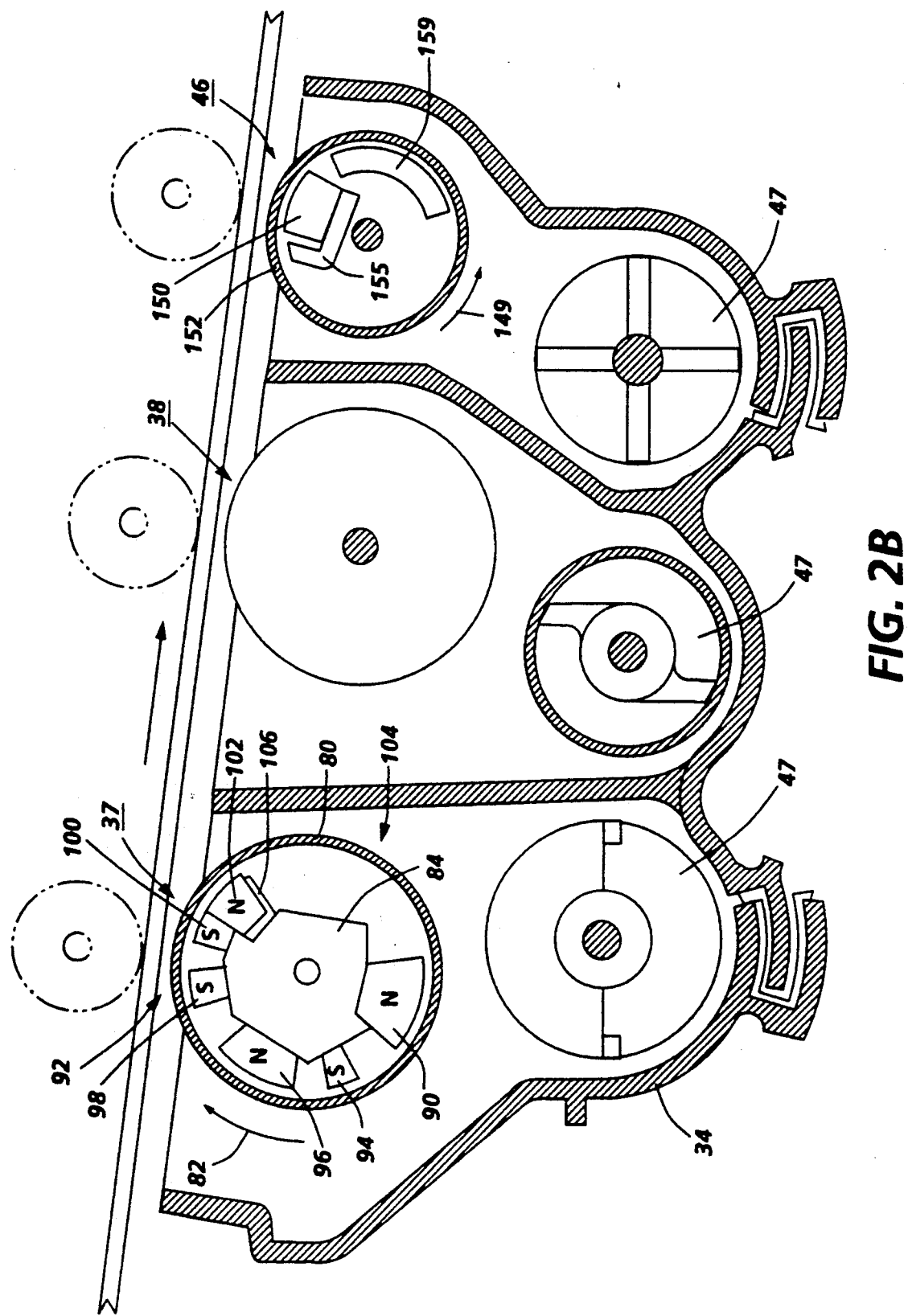

Referring now to the specific subject matter of the present invention, FIGS. 2a and 2b, show developer units 32 and 34 in greater detail. As is apparent developer rollers 37 and 38 of developer unit 34 are substantially identical to one another so only developer roller 37 will be described.

Continuing with the conventions used to illustrate electrographic printing machines, developer roller 37 advances the black developer material into contact with the electrostatic latent image recorded on the photoconductive surface of belt 10. As previously indicated, developer roller 37 is electrically biased so that the highly charged image areas of the latent image attract developer material thereto. Developer roller 37 includes a non-magnetic tubular member or sleeve 80 preferably made from aluminum having the exterior surface thereof roughened. Sleeve 80 rotates in the direction of arrow 82. A magnet assembly 84 is mounted interiorly of roller 50 and spaced therefrom. Magnet assembly 84 is stationary and positioned to attract the developer material to the lower exterior circumferential surface of sleeve 80. In this way, as sleeve 80 rotates in the direction of arrow 82, beads are attracted to the exterior circumferential surface by the so-called pick-up magnet 90 which, in this example is oriented with an N-magnetic polarity. Thus, beads with toner triboelectrically attracted thereto are magnetically attracted to the sleeve 80 which rotates to mechanically transport developer material (beads and toner) into the development zone 92.

Specifically, the beads attracted to the sleeve 80 by the pickup magnet 90 magnetically attach to the sleeve. Then, the magnetic fields from the so-called transport pole 94, which in this example has a south magnetic polarity urge the continued adherence of the beads to the roller. As the beads continue to adhere to the turning sleeve 80, the carriers pass through the magnetic field of the so-called "trim-pole" 96 which is usually used in conjunction with a trim blade or bar (not shown) to regulate or trim the amount of developer material passing to the development zone 92. Magnet assembly 84 is positioned so that two small magnetic poles 98 and 100 of the same polarity are located substantially in the center of the development zone. The magnetic poles on magnets 98 and 100 are located opposed from the photoconductive surface in the region of the gap between sleeve 80 and surface 10.

As the carrier and remaining toner pass the development zone, the so-called "bead carryout pole or magnet" 102 acts to strongly bond the beads to the sleeve 80. But, as the roller continues to turn, the beads reach an area 104, where the gravitational force and the centripetal forces generally overcome the magnetic bonds holding the beads to the roller. This area 104 is often referenced as the bead release zone or point.

As is well known, the placement of two identical polarity oriented magnets adjacent or contiguous to one another results in a magnetic field which has no field reversal and thus always has some potential within finite distances. In roller 37 of FIG. 2B, this condition is present between magnets 90 and 102. Beads on the sleeve 80, could remain on the sleeve past the release area 104 if gravity and centrifrical force are insufficient to overcome the magnetic beads for a particular bead. This occurrence causes a reduction in toner delivered to the photoconductive surface and could affect print quality. Of greater concern is the reverse operation of the developers when the sleeves are to be free of developer material. The orientation of the these magnets urges developer material (i.e. carriers with toner) to be attracted to the sleeve 80 and for some beads to be magnetically bound to the sleeve 80 and pass through the development zone 92. Applicants have found that placing ferromagnetic shunt 106 adjacent magnet 102 have placed and overcome these problems. The shunt 106 is oriented to attenuate the magnets field between magnet 102 and magnet 90. The positioning of the shunt 106 not only improves bead carrier release in normal operation, but reduces the number of beads adhering to the sleeve 80 during reversed rotation of the developers. The magnetic field strength at the bead release zone 104 is still not zero, but it is substantially reduced to effect these advantages.

Applicants have used cold rolled steel with a permeability of at least 2000 or greater of at least approximately 1 to 3 mm. thick with a thickness of 1.5 mm. being preferred for forming these shunts. Generally, the shunt 106 has first and second sides disposed around the magnet 102 to provide the discussed features. The magnets of the unit 84 are generally formed of a rubber or plastic material and embedded in foam in a standard fashion. The magnetic units 84 within the sleeves 80 can be formed in a variety of manners including, by way of example, that disclosed in U.S. Pat. Nos. 4,517,719 and 4,640,808.

Like developer rollers 37 and 38, developer rollers 35 and 36 of developer unit 32 are substantially identical to one another so only developer roller 35 will be described. Developer roller 35 advances the nonblack developer material into contact with the electrostatic latent image recorded on the photoconductive surface of belt 10. As previously indicated, developer roller 35 is electrically biased so that the discharged image areas of the latent image attract developer material thereto. Developer roller 35 includes a non-magnetic tubular member or sleeve 51 preferably made from aluminum having the exterior surface thereof roughened. Sleeve 51 rotates in the direction of arrow 83. A magnet assembly 85 is mounted interiorly of sleeve 51 and spaced therefrom. Magnet assembly 85 is stationary and positioned to attract the developer material to the exterior circumferential surface of sleeve 51. In this way, as sleeve 51 rotates in the direction of arrow 83, developer material is attracted to the exterior circumferential surface by the so-called pickup magnet 91 and moved into the development zone 93 by fields generated by transport magnet 95 and trim magnet 97. Magnet 99 is positioned so that a slot which is machined on its top and extends its full length is located substantially in the center of the development zone.

Further, like roller 37, roller 35 has a carryout magnet 101 to retain beads as they exit the development zone. Generally, as with roller 37, the area along the sleeve 51 designated 103 defines the bead release area where the beads no longer adhere to the sleeve 51. However, unlike roller 37, roller 35 has a magnet, a so-called power shunt magnet 105, disposed between magnets 91 and 101. The magnet 105 operates to ensure that the field between the carryout magnet 101 and the pickup magnet 91 reaches a zero force potential. To increase the width of the release zone 103 and minimize the field strength between magnets 101 and 105, a shunt 107 is placed around the carryout magnet 101. Shunt 107 is essentially identical to shunt 106 in both structure and purpose. Thus, the shunt 107 attenuates the magnetic field in the bead release zone 103 to promote bead release during normal rotation and to inhibit bead attraction and adherence in reverse operation of roller 51.

Figure 3:
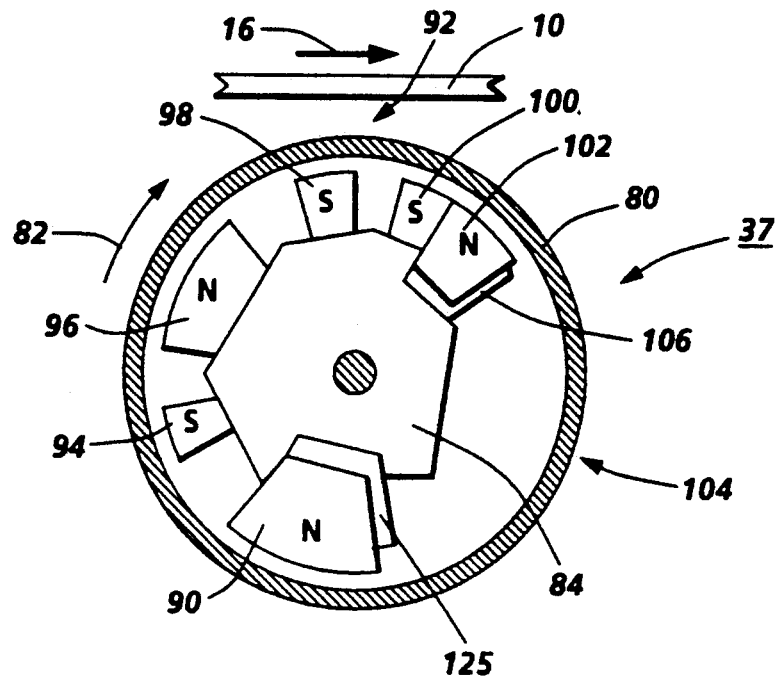
FIG. 3 is an elevational view showing alternative embodiment of one of the developer rollers used in the first developer unit of the FIG. 1 printing machine.

As shown in FIG. 3, a developer roller 37 with a magnetic unit 84 is shown which is substantially identical to the roller 37 of FIG. 2B. In fact, they correspond except that a shunt 125 has been positioned around pick-up magnet 90. This shunt coupled with the previously discussed shunt 106 further ensures that the magnetic field holding the carrier beads to the sleeve 80 after passing the carryout magnet 102 in normal operation and the magnetic field urging pick up and adherence of carrier beads during reverse rotation are insufficient to accomplish same.

Figure 4:
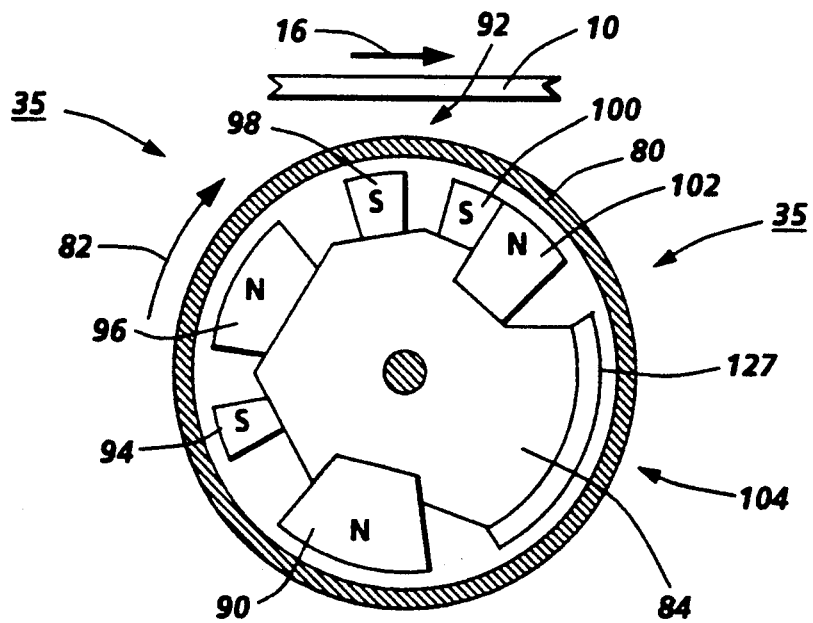
FIG. 4 is another view showing alternative embodiment of one of the developer rollers used in the first developer unit of the FIG. 1 printing machine.

FIG. 4 also shows a roller 35 which is substantially identical to roller 35 of FIG. 2A, save the shunt 106 of FIG. 2A has been removed and replaced by arc shunt 127, which is disposed between the pick-up pole 90 and the bead carryout magnet 102. The shunt 127 attenuates the of magnetic field in the bead release zone 104 while having minimal effect upon the magnetic fields regulating bead transport, trim, development and carryout.

Referring again to FIGS. 2A and 2B, the bead removal devices 44 and 46 are shown with developer units 32 and 34, respectively. These devices are substantially identical so corresponding numbers will be used to identify identical parts of these figures. Specifically, bead removal devices 44 and 46 embodying the present invention which generally rotate in the direction indicate by arrows 148 and 149 (i.e., opposite the direction of the developer rollers 34, 35, 37 and 38) are shown with magnet 150 disposed in a fixed relationship with the belt 10. The magnets 150 are stationary and disposed within rotating housing 152. Shunts 155 are disposed within the housings 152 to shape the magnetic fields generated by the magnets 150 in selected directions. Further, shunts 157 and 159 are positioned in conjunction with the magnets 150 and shunts 155 so the magnetic field from each magnet is attenuated in all but those directions generally radiating toward the belt 10.

Shunts 155 and 157 of BRD 44 and shunts 155 and 159 of BRD 46 are preferably formed of a ferromagnetic material (e.g. cold rolled steel with a thickness greater than 1 mm). The magnets 110 are ordinarily so-called rare earth magnets. The magnets and shunts may be held in place by foam in a fashion similar to that discussed with magnetic units 84 and 85.

As will be appreciated, except for the portions of the shell proximate the photoconductive surface and the portions immediately adjacent thereto the magnetic field strength along the bead removal device's housing 150 is minimized by the disclosed arrangement. The optimal arrangement is dependent in part upon the characteristics of the developer and ambient conditions. Generally, applicants have found that the shunts 157 and 159 should be formed of cold rolled steel with a permeability of greater than 1500 and preferably approximately 2000 with a thickness of at least 1 mm or more. Applicants have also found that the forming of shunts 157 and 159 as arc shunts with a radius proportional to the BRD's shell provides a greater effectiveness, although ferromagnetic strips have been employed. Generally then, with the disclosed arrangement of shunts and magnets, beads will be attracted to the BRD from the belt 10 and then deposited in a sump or reservoir. Further, beads in the sump will not be attracted to the BRD and will not become attached thereto. These conditions prevail whether the BRD is being rotated in a normal or reverse fashion. Thus, the formation of bead chains are substantially hindered and operation of the BRD in either direction will have minimal effect upon its function of "capturing" beads on the photoconductive surface and depositing such beads in the sump or reservoir.

Figure 5A:
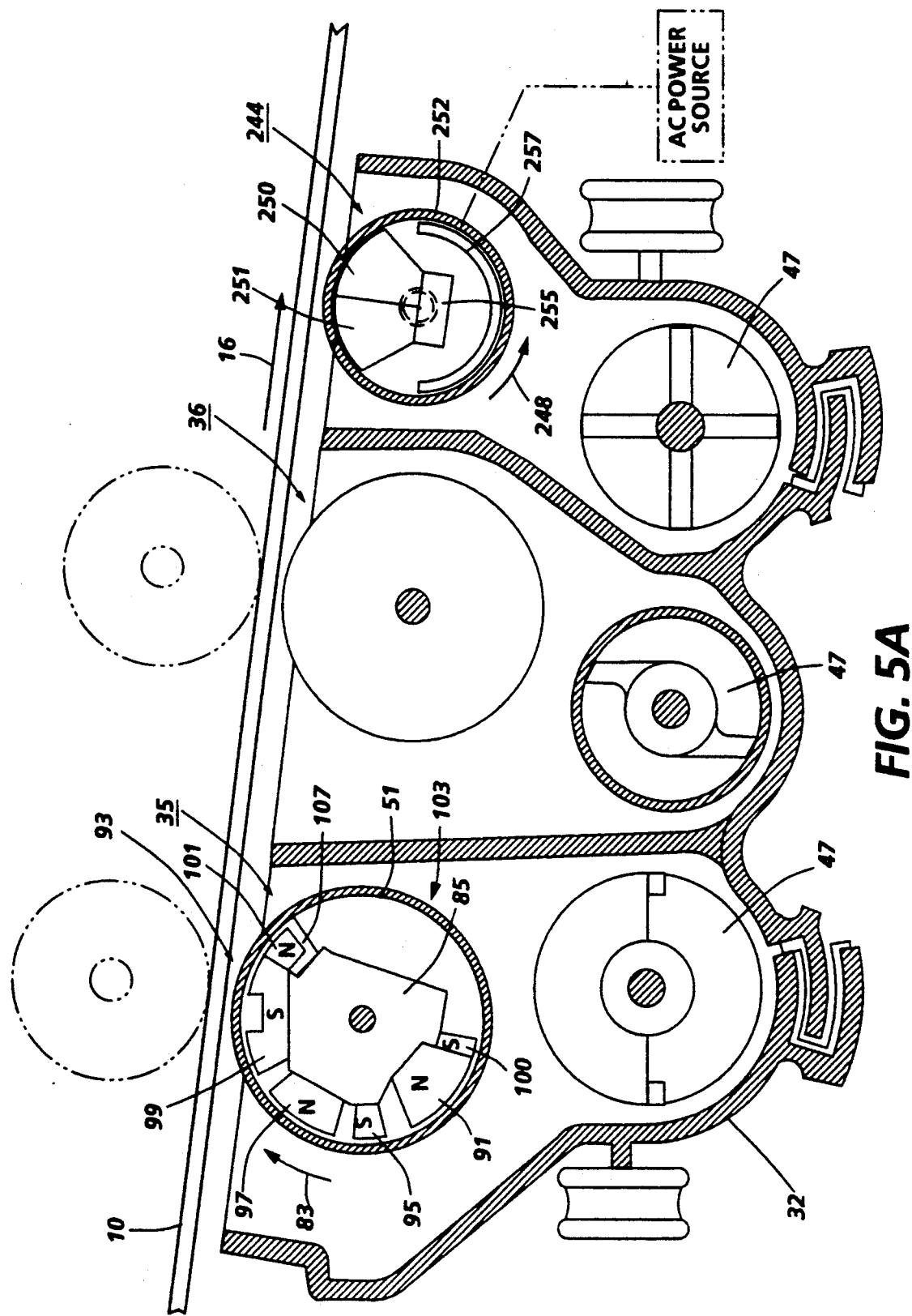
FIG. 5a and 5b are elevational views showing alternative developer units and a portion of the photoconductive surface of the FIG. 1 printing machine.
Figure 5B:
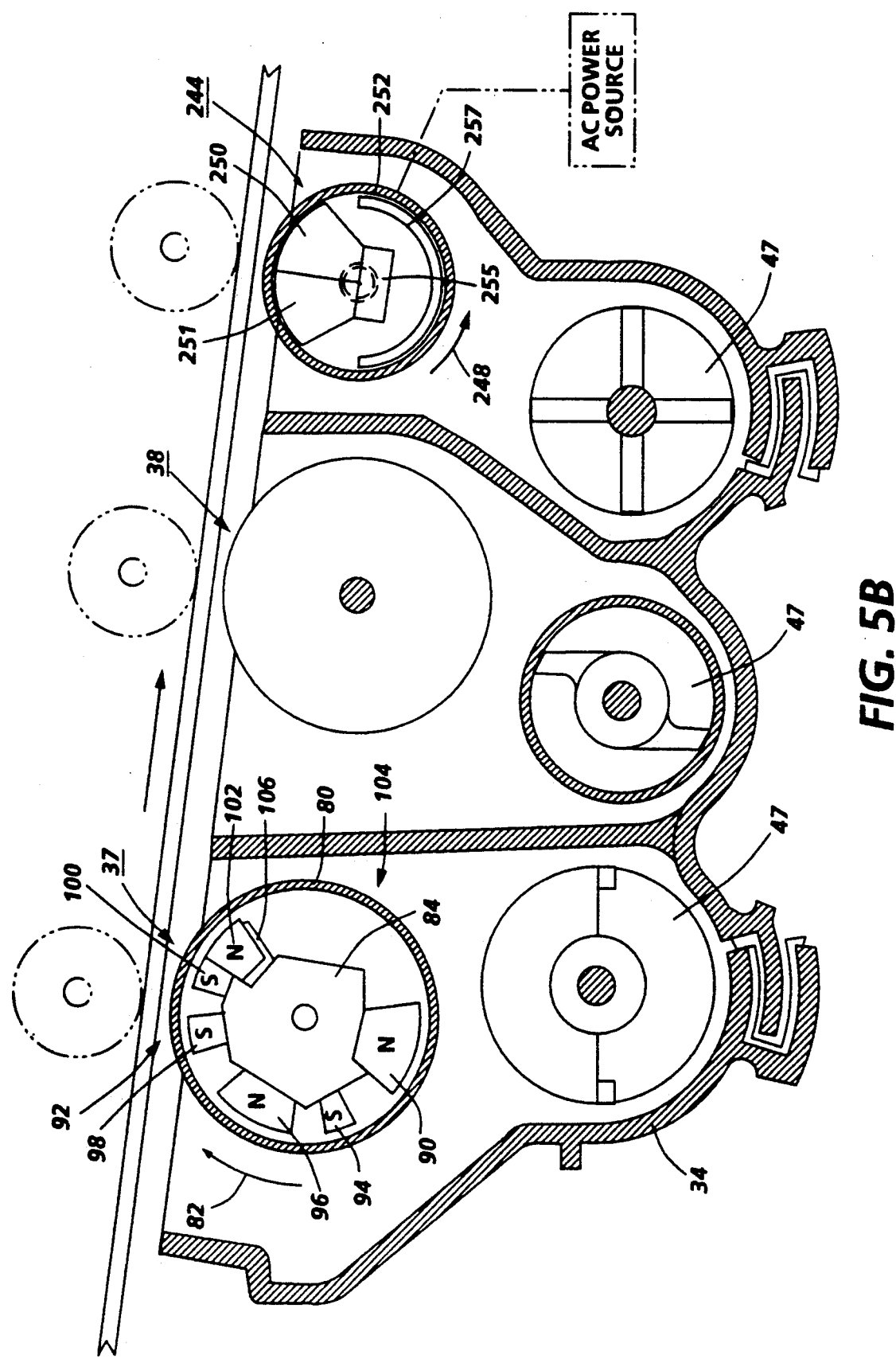
Figure 6:
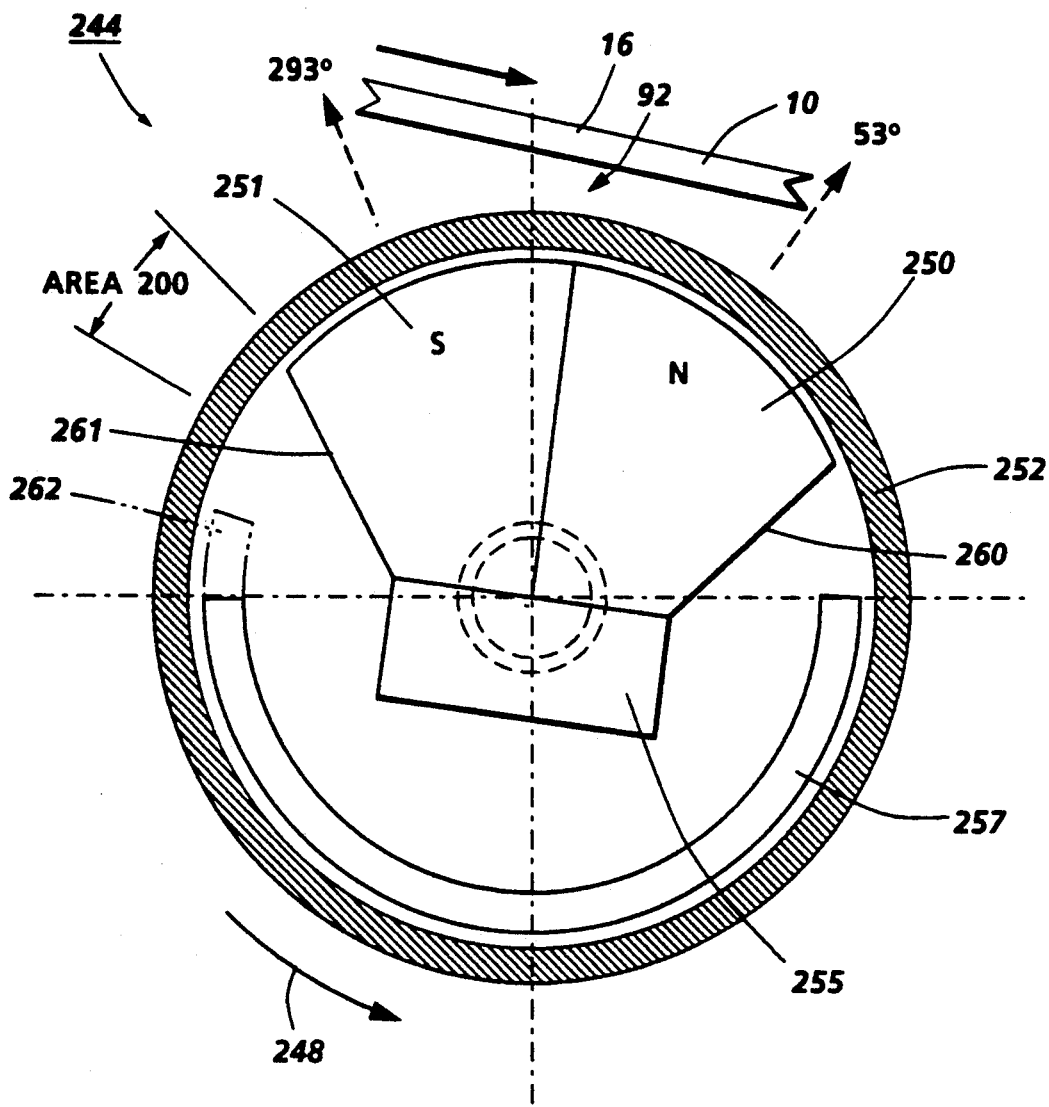
FIG. 6 is an elevational view showing the bead removal device of the developer unit and a portion of the photoconductive surface of FIGS. 5a and 5b.

FIGS. 5A and 5B show views of developer units similar to those of FIGS. 2A and 2B and in accordance with the present invention. Substantially identical portions of these referenced figures are commonly numbered for ease of understanding. For example, the developer rollers 35 and 37 of FIGS. 5A and 5B are identical to those of FIGS. 2A and 2B. The bead removal devices 244 and 246 as shown with the developer units 32 and 34, respectively, are not, however, identical to the devices 44 and 46 of FIGS. 2A and 2B. The bead removal devices 244 and 246 are rotationally driven by actuation means not seen. Applicants prefer that such rotation be opposite the direction of the rotation of the developer rollers 34, 35, 37 and 38 as indicated by arrow 248 and 249, but this is not essential. These bead removal devices 244 and 246 are substantially identical so corresponding numbers will be used to identify identical parts therein. Reference may also be made to FIG. 6 which is view of the bead removal device 244.

Magnets 250 and 251 are disposed in a fixed relationship with the belt 10. The magnets 250 and 251 are, thus, stationary within each of the housings 252 which rotate. Shunts 255 are disposed within the housings 252 to shape the magnetic fields generated by the magnets 250 and 251 in selected directions. Further, shunts 257 are positioned in conjunction with the magnets 250 and 251 and shunts 255 so the magnetic field from the magnets is attenuated in all but those directions generally radiating toward the belt 10.

Shunts 255 and 257 of the bead removal devices 244 and 246 are preferably formed of a ferromagnetic material (e.g. low carbon cold rolled steel with a thickness greater than 1 mm and preferably approximately 1.6 mm thick). The permeability of the material used is approximately 1000 and preferably between 180 and 2000. The magnets 150 and 151 are of substantially opposite polarity relative to their positioning within the housing 252. The magnets are preferably a Neodymium Iron Boron alloy (NIB) available from Delco-Remy (a division of General Motors Corporation). It will be appreciated that other materials can be used to accomplish substantially the same results. The magnets and shunts may be held in place by foam in a fashion similar to that discussed with magnetic units 84 and 85, previously.

As stated above, the magnets 250 and 251 are arranged in approximate opposite polarity orientation. That is one magnet has a north pole of approximately opposite orientation of the north pole of the other so that the magnets 250 and 251 do not repel but rather attract each other. Applicants have found that the maximum force across the nip between the shell and the surface is yielded by magnetic vectors of the two magnets being offset between approximately 140° to 100° and preferably 120° (See FIG. 5, wherein the north poles of magnet 250 and 251 are at 53° and 293°, respectively, so that in the example only 60° separate the opposite polls adjacent the surface 10.). Further, it has been found that magnetic fields radiating in directions away from the surface 10 in the shown configuration are minimized when the walls 260 and 261 of magnets 250 and magnets 250 and 251 are formed approximately parallel to the magnetic polar axis of the magnets 250 and 251, respectively.

Applicants have discovered that in some cases, arc shunt 257 should extend in a direction further toward the photoconductive surface 10. It has been found that due to the proximity of the developer rollers 36 and 38 to bead removal devices 244 and 246, respectively, the magnetic fields between them can inhibit and affect their respective functions. Generally, in such cases the shunt 257 would extend in an arc between 5° and 20°, as shown by the phantom section 265. This and the shaped walls 260 and 261 substantially eliminate magnetic interference or cross talk between the bead removal device and developer roller. Applicants have also discovered that in many instances application of an AC current to the housing 252 substantially increase the bead removal efficiency of the bead removal devices 244 and 246. Applicants have found that the voltage applied should be between 1000 and 3000 volts peak to peak and preferably approximately 2000 volts of a low amperage AC signal.

Applicants have further discovered that the described embodiment of the invention has other substantive advantages. For example, during use of this device, applicants have found bead carriers building up in the area designated 200 and remaining in this area as the bead removal device rotates between approximately 5 and 100 revolutions per minute and preferably approximately 50. This build up of bead carriers tend to act as a brush to loosen toner particles on the housings 252 so that it drop into the area about augers 47. This feature avoids the problem of release of charged toner occurring with the impact of bead carriers with the bead removal device, which after release in this manner could settle on the photoconductive surface to thereby adversely affect image quality.

The developer unit, develops the imaged areas of the latent image with toner as the photoconductive surface passes the unit. The developer unit has at least one developer roller which has magnetic means positioned therein for generating a magnetic field extending therefrom. The shaped magnetic fields extending from the roller are shaped by the positioning of magnets and magnetic field shapers. The magnetic fields enhance the operation of the roller including the pick-up, the transport, the delivery to the development zone, the retention beyond the development zone and the release into the sump of the carrier beads. Further, the developer units include bead removal devices which comprise an outer roller housing, fixed magnets which operates to attract bead carriers adhering to the bead removal device from the photoconductive surface and to deposit the carriers in a sump. The bead removal device means comprise a double shunt and magnet field source generator arranged to produce magnetic fields shaped for attracting and releasing carriers in predetermined areas.

It is, therefore, apparent that there has been provided in accordance with the present invention, a developer unit for use in an electrophotographic printing machine that fully satisfies the aims and advantages hereinbefore set forth. While this invention has been described in conjunction with a preferred embodiment thereof, it is evident that many alternatives, modifications, and variations will be apparent to those skilled in the art. Accordingly, it is intended to embrace all such alternatives, modifications and variations that fall within the spirit and broad scope of the appended claims.

We claim:

1. An apparatus for developing a latent image recorded on a moving photoconductive surface comprising:
    means for moving magnetic carrier beads having toner particles adhering triboelectrically thereto to a development zone proximate to the photoconductive surface so that the latent image attracts toner particles from the carrier beads thereto;
    magnetic means, generating a magnetic field, for attracting magnetic carrier beads proximate the photoconductive surface after passing through the development zone and moving such carrier beads to a release zone;
    first magnetic field shaping means, coupled to said magnetic means for enhancing the magnetic field generated by said magnetic means in a direction toward the photoconductive surface and for attenuating the magnetic field in the release zone so that substantially all the carrier beads moved to the release zone are released from said magnetic means; and
    second magnetic field shaping means positioned proximate to said magnetic means for attenuating the magnetic field generated by said magnetic means in an area after the release zone to release the carrier beads adhering to the magnetic means after passing through the release zone.

2. The apparatus of claim 1 wherein said magnetic means include:
    a rotating outer shell positioned downstream from the development zone and adjacent the photoconductive surface; and
    a fixed position magnet disposed within said shell for generating the magnetic field.

3. The apparatus of claim 2 wherein said first magnetic field shaping means is a stationary ferromagnetic strip disposed within said shell for attenuating the magnetic field of said fixed position magnet in generally a first and second direction and for enhancing the magnetic field in a third direction toward the photoconductive surface.

4. The apparatus of claim 3 wherein said shell is a tubular member and said second magnetic field shaping means is a ferromagnetic strip disposed within said shell for attenuating the magnetic field emanating from said magnet in generally a fourth direction so that said ferromagnetic strips enhance the generated magnetic field in the direction generally toward the photoconductive surface and attenuate the generated magnetic field in substantially all other radial directions with respect to said tubular member.

5. The apparatus of claim 2, wherein said shell is a tubular member and said first and second magnetic field shaping means are a first and second ferromagnetic strip bounding said magnet to enhance the magnetic field in a direction toward the photoconductive surface and to attenuate the magnetic field emanating from said magnet in substantially all other radial directions with respect to said tubular member.

6. The apparatus of claim 4 wherein said first ferromagnetic strip has an L-shaped cross-section with a first leg upon which the magnet is disposed and with a second leg extending toward the photoconductive surface and said second ferromagnetic strip has an arc shaped cross-section and is positioned along a wall of said tubular member on the side of said magnet opposite the second leg of said first ferromagnetic strip.

7. The apparatus of claim 5, wherein said ferromagnetic strips have a thickness of substantially 1 mm or larger and a magnetic permeability of substantially 2,000 gauss or greater.

8. A method of developing a latent image recorded on a moving photoconductive surface comprising the steps of:
    moving magnetic carrier beads having toner particles adhering triboelectrically thereto to a development zone proximate to the photoconductive surface so that the latent image attracts toner particles from the carrier beads thereto;
    positioning a cylindrical housing downstream from the development zone adjacent the photoconductive surface;
    generating, in a cleaning zone, a magnetic field from within the cylindrical housing, for attracting magnetic carrier beads adhering to the photoconductive surface after the photoconductive surface passes through the development zone, and moving such carrier beads to a release zone;

decreasing the magnetic field intensity in the release zone so as to release substantially all of the carrier beads from the cylindrical housing; and reducing the magnetic field generated in a region between the release zone and the cleaning zone to release the carrier beads in this region to limit carrier bead attraction and adhesion on the housing in all areas remote from the photoconductive surface.

9. An apparatus for developing a latent image recorded on a moving photoconductive surface comprising:

means for delivering magnetic carrier beads having toner particles adhering triboelectrically thereto to a development zone proximate to the photoconductive surface so that the latent image attracts toner particles from the carrier beads thereto;

a bead removal device positioned adjacent the photoconductive surface and downstream from the development zone;

said device having a rotatable outer shell and fixed magnetic means positioned within the shell;

a first magnetic shunt disposed in the shell to shape the magnetic field to urge capture of any beads passing between the photoconductive surface and the bead removal device and to urge release of such captured carriers into a sump as the shell rotates; and a second magnetic shunt positioned to shape the magnetic field to urge release of beads captured during reverse rotation of the shell and to shape the magnetic field to minimize the magnetic field on a portion of the shell to inhibit bead chain formation.

10. An apparatus for developing a latent image recorded on a moving photoconductive surface, comprising:

a developer roller for developing the latent image with toner of predetermined polarity, said roller being selectively rotatable in a first direction and in a second direction reversed from the first direction;

magnetic means for generating a magnetic field, said magnetic means being mounted stationarily interiorly of said roller;

ferromagnetic field shaping means disposed within said roller to shape the magnetic fields induced by the magnetic means, said field shaping means being mounted stationarily interiorly of said roller;

said magnetic means and said field shaping means being positioned to attract carrier beads having toner adhering triboelectrically thereto for delivery to a development zone and to release the carrier beads from the roller in a release zone during rotation of said roller in the first direction and to inhibit transporting carrier beads through the development zone during rotation of said roller in the second direction; and a bead removal device positioned adjacent the photoconductive surface and downstream from the development zone, said device having a rotatable outer shell and fixed magnetic means positioned within the shell, a first magnetic shunt disposed in the shell to shape the magnetic field to urge capture of any beads passing between the photoconductive surface and the bead removal device and to urge release of such captured carriers into a sump as the shell rotates, and a second magnetic shunt positioned to shape the magnetic field to urge release of beads captured during reverse rotation of the shell and to shape the magnetic field to minimize the magnetic field on a portion of the shell to inhibit bead chain formation.

11. An apparatus for developing a latent image recorded on a moving photoconductive surface comprising:

magnetic means, generating a magnetic field, for attracting and moving magnetic carrier beads having toner particles adhering triboelectrically thereto to a development zone proximate to the photoconductive surface so that the latent image attracts toner particles from the carrier beads thereto;

magnetic field shaping means, coupled to said magnetic means, for attenuating the magnetic field generated by said magnetic means after the development zone so that the carrier beads release from said magnetic means after passing through the development zone;

second magnetic means, generating a second magnetic field, for attracting magnetic carrier beads proximate the photoconductive surface after passing through the development zone and moving such carrier beads to a release zone;

second magnetic field shaping means, coupled to said second magnetic means for enhancing the second magnetic field generated by said second magnetic means in a direction toward the photoconductive surface and for attenuating the second magnetic field in the release zone so that substantially all the carrier beads moved to the release zone are released from said second magnetic means; and third magnetic field shaping means positioned proximate to said second magnetic means for attenuating the second magnetic field generated by said second magnetic means in an area after the release zone to release the carrier beads adhering to the magnetic means after passing through the release zone.

12. An apparatus for developing a latent image recorded on a moving photoconductive surface comprising:

means for moving magnetic carrier beads having toner particles adhering triboelectrically thereto to a development zone proximate to the photoconductive surface so that the latent image attracts toner particles from the carrier beads thereto;

magnetic means, generating a magnetic field, for attracting magnetic carrier beads proximate the photoconductive surface after passing through the development zone and moving such carrier beads to a release zone, said magnetic means includes a first and a second magnetic field sources positioned contiguous to one another and having substantially opposite polarity orientations for generating the magnetic field for attracting carrier beads proximate the photoconductive surface; and a housing in which said moving means and magnetic means are positioned.

13. The apparatus of claim 12 wherein said magnetic means further includes a rotating outer shell positioned downstream from the development zone and proximate to the photoconductive surface and said first and second magnetic field source means are stationary permanent magnets disposed within said shell.

14. The apparatus of claim 13 wherein said shell is a tubular member, and said first and second stationary permanent magnets each having a surface proximate the photoconductive surface which is arcshaped and each having a surface opposite the adjacent sides of said magnets which is substantially parallel with the magnetic polar axis of each of said magnets.

15. An apparatus for developing a latent image recorded on a moving photoconductive surface comprising:
    means for moving magnetic carrier beads having toner particles adhering triboelectrically thereto to a development zone proximate to the photoconductive surface so that the latent image attracts toner particles from the carrier beads thereto;
    magnetic means, generating a magnetic field, for attracting magnetic carrier beads proximate the photoconductive surface after passing through the development zone and moving such carrier beads to a release zone, said magnetic means includes a first and a second magnetic field source positioned adjacent one another and having substantially opposite polarity orientations for generating the magnetic field for attracting carrier beads proximate the photoconductive surface, wherein said magnetic means further includes a rotating outer shell positioned downstream from the development zone and proximate to the photoconductive surface and said first and second magnetic field source means are stationary permanent magnets disposed within said shell and a first and second ferromagnetic strip disposed generally on the sides of the first and second magnetic means opposite the photoconductive surface to enhance the magnetic field generated by the first and second permanent magnets in a direction toward the photoconductive surface and to attenuate the magnetic field emanating from said magnets in substantially all other radial directions; and
    a housing in which said moving means and magnetic means are positioned.

16. The method of claim 8 further comprising the step of cleaning the cylindrical housing.

17. A method of developing a latent image recorded on a moving photoconductive surface, comprising the steps of:
    moving magnetic carrier beads having toner particles adhering triboelectrically thereto to a development zone proximate to the photoconductive surface so that the latent image attracts toner particles from the carrier beads thereto;
    positioning a cylindrical housing downstream from the development zone adjacent the photoconductive surface;
    generating, in a cleaning zone, a magnetic field from within the cylindrical housing, for attracting magnetic carrier beads adhering to the photoconductive surface after the photoconductive surface passes through the development zone, and moving such carrier beads to a release zone;
    decreasing the magnetic field intensity in the release zone so as to release substantially all of the carrier beads from the cylindrical housing;
    reducing the magnetic field generated in a region between the release zone and the cleaning zone to release the carrier beads in this region to limit carrier bead attraction and adhesion on the housing in all areas remote from the photoconductive surface; and
    cleaning the cylindrical housing wherein the step of moving includes rotating the cylindrical housing and the step of cleaning includes retaining carrier beads in a substantially constant position to act as a brush as the cylindrical housing rotates.

18. A method of developing a latent image recorded on a moving photoconductive comprising the steps of:
    moving magnetic carrier beads having toner particles adhering triboelectrically thereto to a development zone proximate to the photoconductive surface so that the latent image attracts toner particles from the carrier beads thereto;
    positioning a cylindrical housing downstream from the development zone adjacent the photoconductive surface;
    generating a magnetic field from within the housing;
    attracting magnetic carrier beads from the photoconductive surface proximate a portion of the housing;
    moving the attracted carrier beads to a release zone away from the photoconductive surface which includes rotating the housing;
    attenuating the magnetic field generated in the area of the housing away from the photoconductive surface to promote release of the attracted carrier beads in the release zone and to limit carrier bead attraction and adhesion on the housing in all areas away from the photoconductive surface;
    cleaning the housing which includes retaining carrier beads in a substantially constant position to act as a brush as the housing rotates;
    enhancing the magnet field generated in the area of the housing proximate the photoconductive surface to encourage migration of carrier beads from the photoconductive surface to the housing so that said step of shaping the generated magnetic field and said step of attenuating the generated magnetic field include inhibiting carrier beads from moving proximate the photoconductive surface when said cylindrical housing is rotated in a reverse angular direction.

* * * * *